United States Patent [19]

Farid et al.

[11] Patent Number: 4,743,529

[45] Date of Patent: May 10, 1988

[54] NEGATIVE WORKING PHOTORESISTS RESPONSIVE TO SHORTER VISIBLE WAVELENGTHS AND NOVEL COATED ARTICLES

[75] Inventors: Samir Y. Farid, Rochester; Neil F. Haley, Fairport; Roger E. Moody; Donald P. Specht, both of Rochester, all of N.Y.

[73] Assignee: Eastman Kodak Company, Rochester, N.Y.

[21] Appl. No.: 933,658

[22] Filed: Nov. 21, 1986

[51] Int. Cl.[4] .................................................. G03C 1/76
[52] U.S. Cl. .................................... 430/281; 430/286; 430/287; 430/919; 430/920; 522/25
[58] Field of Search ............... 430/281, 920, 919, 271, 430/286, 287; 522/25

[56] References Cited

U.S. PATENT DOCUMENTS

Re. 27,922 2/1974 Heseltine et al. ................... 96/35.1
Re. 27,925 2/1974 Jenkins et al. ...................... 96/35.1

FOREIGN PATENT DOCUMENTS 2083832A 9/1981 United Kingdom ................ 430/920

OTHER PUBLICATIONS

Specht, Martic, and Farid, "A New Class of Triplet Sensitizers", *Tetrahedron*, vol. 38, pp. 1203–1211, 1982.
Research Disclosure, vol. 200, Dec. 1980, 20036.

*Primary Examiner*—Jack P. Brammer
*Attorney, Agent, or Firm*—Carl O. Thomas

[57] ABSTRACT

A negative working photoresist is disclosed responsive to imaging radiation of a visible wavelength shorter longer than 550 nm comprised of an organic film forming component containing ethylenic unsaturation and capable of selective immobilization by addition at the site of ethylenic unsaturation and activator and photosensitizer coinitiators for ethylenic addition. The activator is an azinium salt activator, and the photosensitizer is a dye having its principal absorption peak at a wavelength shorter than 550 nm and having a reduction potential which in relation to that of said azinium salt activator is at most 0.1 volt more positive. When the dye is a keto dye, it exhibits when excited by imaging radiation an intersystem crossing efficiency to a triplet state of less than 10 percent.

29 Claims, No Drawings

NEGATIVE WORKING PHOTORESISTS RESPONSIVE TO SHORTER VISIBLE WAVELENGTHS AND NOVEL COATED ARTICLES

FIELD OF THE INVENTION

This invention relates to photography. More specifically, this invention relates to novel photoresist compositions and to novel coated articles containing these photoresist compositions.

BACKGROUND OF THE INVENTION

Commercially available compositions serving a variety of industrial needs for creating image patterns have become recognized as a distinct class of materials, referred to as photoresists. Photoresists are typically coated or otherwise spatially positioned, imagewise exposed to actinic radiation, and developed to leave the photoresist selectively in either exposed or unexposed areas. The name "photoresist" originated from the use of material remaining after imaging and development to resist etching and thereby define an etching pattern. However, today photoresists are employed for many divergent applications, including the formation of totally exposed layers, such as planarizing layers, and producing colored images.

Negative working photoresists are those which upon development are retained in areas exposed to actinic radiation. Negative working photoresists characteristically include an organic film forming component exhibiting ethylenic (vinyl) unsaturation. The film forming component is rendered immobile on development by undergoing photoinduced addition reactions at the ethylenic unsaturation sites.

The film forming components containing ethylenic unsaturation generally exhibit limited direct response to imaging radiation and therefore rely on one or more initiators for the ethylenic addition reaction. Heseltine et al and Jenkins et al U.S. Pat. No. Res. 27,922 and 27,925 disclose N-oxyazinium initiators for photocrosslinking and photopolymerization, respectively.

It is common practice in preparing photoresist compositions to employ coinitiators. One of the coinitiators is a photosensitizer. Photosensitizers are relied upon to capture photons of exposing radiation. The remaining coinitiator is referred to as an activator. The activator is not relied upon to respond directly to exposing radiation, but rather adjacent activator and photosensitizer molecules react, following excitation of the latter by photon capture, causing release of a free radical which in turn induces immobilizing addition reactions at sites of ethylenic unsaturation.

It is generally accepted that photosensitizer coinitiators function by photon absorption to lift an electron from an occupied molecular orbital to a higher energy, unoccupied orbital. The spin of the electron lifted to the higher energy orbital corresponds to that which it exhibited in its original orbital or ground state. Thus, the photosensitizer in its initially formed excited state is in a singlet excited state. The duration of the singlet excited state is limited, typically less than a few nanoseconds. The excited photosensitizer can return from its singlet excited state directly to its original ground state, dissipating the captured photon energy. Alternatively, the singlet excited state photosensitizer in some instances undergoes intersystem crossing through spin inversion to another excited state, referred to as a triplet state, wherein lifetimes are typically in the microsecond to millisecond range. Since photosensitizer coinitiators which exhibit triplet states remain in an excited state for time periods that are orders of magnitude greater than photosensitizer coinitiators which exhibit only singlet excited states, a much longer time period is available for reaction with the paired activator coinitiator.

Specht and Farid U.K. No. 2,083,832A discloses photopolymerization coinitiators including azinium activators and amino-substituted photosensitizer (e.g., amino-substituted ketocoumarin) coinitiators which exhibit triplet states on excitation. An essentially cumulative disclosure is provided by *Research Disclosure*, Vol. 200, Dec. 1980, Item 20036. *Research Disclosure* is published by Kenneth Mason Publications, Ltd., Emsworth, Hampshire P010 7DD, England. As illustrated by Specht, Martic, and Farid, "A New Class of Triplet Sensitizers", *Tetrahedron*, Vol. 38, pp. 1203-1211, 1982, these amino-substituted 3-ketocoumarins exhibit intersystem crossing efficiencies ranging well above 10 percent—e.g., from 0.18 to 0.92 or 18 to 92 percent, measured in polymer.

In concurrently filed, commonly assigned patent application, Ser. No. 933,660, titled NEGATIVE WORKING PHOTORESISTS RESPONSIVE TO LONGER WAVELENGTHS AND NOVEL COATED ARTICLES, negative working photoresists are disclosed comprised of a film forming component containing ethylenic unsaturation and capable of selective immobilization as a function of ethylenic addition, and activator and photosensitizer coinitiators for ethylenic addition. The activator is an azinium salt, and the photosensitizer is a dye having its principle absorption peak at a wavelength longer than 550 nm and having a reduction potential which in relation to that of the azinium salt activator is at most 0.1 volt more positive.

In concurrently filed, commonly assigned patent application, Ser. No. 933,712, titled DYE SENSITIZED PHOTOGRAPHIC IMAGING SYSTEM, a photographic imaging system comprised of an imaging dye or a precursor thereof, a hardenable organic component containing ethylenic unsaturation sites and capable of imagewise modulating mobility of the dye or dye precursor as a function of addition at the sites of ethylenic unsaturation, and coinitiators for ethylenic addition. The coinitiators are comprised of of an azinium salt activator and a photosensitizer which is a dye exhibiting a reduction potential which in relation to that of said azinium salt activator is at most 0.1 volt more positive, with the further proviso that, when the photosensitizer is a keto dye having its absorption peak at a wavelength shorter than 550 nm, it exhibits when excited by imaging radiation an intersystem crossing efficiency to a triplet state of less than 10 percent.

In concurrently filed, commonly assigned patent application, Ser. No. 933,657, titled ENHANCED IMAGING COMPOSITION CONTAINING AN AZINIUM ACTIVATOR, an imaging composition is disclosed comprised of an organic component containing ethylenic unsaturation sites and capable of selective hardening by addition at the sites of ethylenic unsaturation, an azinium salt activator, a photosensitizer having a reduction potential which in relation to the reduction potential of the azinium salt activator is at most 0.1 volt more positive, and an image enhancing amount of benzene substituted with an electron donating amino group and one or more groups capable of imparting a net Hammett sigma value electron withdrawing characteristic of at least +0.20 volt to said benzene ring.

SUMMARY OF THE INVENTION

In one aspect this invention is directed to a negative working photoresist comprised of an organic film forming component containing ethylenic unsaturation and capable of selective immobilization as a function of ethylenic addition, and coinitiators for ethylenic addition comprised of an azinium salt activator and a photosensitizer. The photosensitizer is a dye having its principal absorption peak at a wavelength shorter than 550 nm and having a reduction potential which in relation to that of the azinium salt activator is at most 0.1 volt more positive. When the dye is a keto dye, it exhibits when excited by imaging radiation an intersystem crossing efficiency to a triplet state of less than 10 percent.

In another aspect this invention is directed to an article comprising a substrate and a coating comprised of a negative working photoresist as described above.

The present invention provides blue and green responsive negative working photoresists which contain novel photosensitizer coinitiators imparting a variety of highly desirable properties. By employing dyes (which by definition are colored) as photosensitizers the photoresists are rendered responsive to the visible spectrum. This allows the photoresists to be imagewise exposed using a master that provides a visible image. By employing the photoresists of this invention in combination with photoresists sensitized to longer wavelengths it is possible to form multicolor images. The dye photosensitizer coinitiators employed in the photoresists of this invention exhibit high levels of stability, including high thermal and storage stability levels. In addition, the photoresists of this invention can be imagewise exposed of visible wavelengths in the blue and green regions of the spectrum.

A notable feature of the photoresists of this invention is that they image efficiently with dyes employed as photosensitizers having their principal absorption peak at a wavelength shorter than 550 nm (hereinafter referred to as shorter wavelength dyes) regardless of the dye class, provided the dye reduction potentials are properly related to that of the azinium salt activator with which they are employed.

A second notable feature is that these shorter wavelength dye photosensitizers have been found to be effective even though they exhibit intersystem crossing efficiencies to a triplet state of less than 10 percent. To the limited extent that the art has previously reported photosensitizer coinitiators for azinium activators consideration has been limited to those photosensitizers which exhibit high intersystem crossing efficiencies to a triplet state. This selection is based on the reasoning that dye photosensitizers with longer lifetimes above the ground state have a better opportunity to transfer energy to the azinium activator coinitiator.

Of known photosensitizer coinitiators the few that have exhibited radiation absorptions extending into the visible spectrum thereby qualifying them to be considered as dyes—specifically, amino-substituted keto coumarin and ketomethylene (i.e., merocyanine), both shorter wavelength keto dyes—have all exhibited high intersystem crossing efficiencies to a triplet state. It has now been observed that shorter wavelength dyes satisfying specified reduction potentials in relation to the azinium activators with which they are employed are generally useful as photosensitizer coinitiators, regardless of the dye class from which they are chosen and regardless of whether they exhibit high or low intersystem crossing efficiencies to a triplet state. This includes the specific recognition that shorter wavelength keto dyes having low efficiency intersystem crossing efficiencies to a triplet state are highly efficient photosensitizer coinitiators for azinium activators. This opens up a much wider choice of shorter wavelength dyes than heretofore have been thought to be useful as photosensitizers with azinium activators for photoimmobilization by initiation of ethylenic addition reactions.

DESCRIPTION OF PREFERRED EMBODIMENTS

It has been discovered that negative working photoresists of the type which undergo immobilization by addition reaction at the site of ethylenic unsaturation can be improved in their performance capabilities by the incorporation of an azinium activator and certain shorter wavelength dyes not heretofore appreciated to be useful as photosensitizer coinitiators. Specifically, it is the recognition of this invention that useful photosensitizers can be selected from any known dye class, provided they exhibit a reduction potential which in relation to that of the azinium activator is at most 0.1 volt more positive.

Dyes satisfying the required reduction potentials can be selected from any of various known shorter wavelength dyes. Among specifically contemplated dye classes from which shorter wavelength dyes can be selected are coumarin (including keto coumarin and sulfonocoumarin) dyes, merocyanine dyes, merostyryl dyes, oxonol dyes, and hemioxonol dyes. Dyes from each of the foregoing classes all contain a keto group in the chromophore and are all therefore designated keto dyes. In addition, it is a specific recognition of this invention that a dye photosensitizer useful in the practice of this invention need not be a keto dye. That is, a keto group in the chromophore of the dye is not essential. Non-keto dyes embrace a variety of dye classes, including non-keto polymethine dyes, anthracene dyes, acridine dyes, aniline dyes, rhodamine, and azo dyes. Non-keto polymethine dyes include cyanine, hemicyanine, and styryl dyes.

Dyes from the various classes noted are in some instances shorter wavelength dyes and in some instances longer wavelength dyes (i.e., dyes having their principal absorption peak at wavelengths longer than 550 nm). Shorter wavelength dyes having their principal absorption peak in the spectral region below 500 nm generally appear yellow and can be easily selected visually. To the extent the absorption of the dye ranges above 500 nm in the green portion of the spectrum, the dyes become magenta in hue. To provide an objective standard for selection, the shorter wavelength dyes employed in the practice of this invention are those which exhibit substantial blue or green absorption and in all instances exhibit maximum absorption in a photoresist coating at wavelengths of less than 550 nm. There are, in addition, general structural correlations that can serve as a guide in selecting dyes from the above classes which are shorter wavelength in hue. For polymethine dyes, generally the shorter the methine chain, the shorter the wavelength of the absorption peak. Nuclei also influence absorption. The addition of fused rings to nuclei tends to favor longer wavelengths of absorption. Substituents can also alter absorption characteristics. In the formulae which follow, unless otherwise specified, alkyl groups and moieties contain from 1 to 20 carbon atoms, preferably from 1 to 8 carbon atoms. Aryl groups and moieties contain from 6 to 15 carbon atoms and are preferably phenyl or naphthyl groups or moieties.

Preferred shorter wavelength cyanine dyes are monomethine cyanines; however, useful shorter wavelength cyanine dyes can be selected from among those of Formulae 1 and 2.

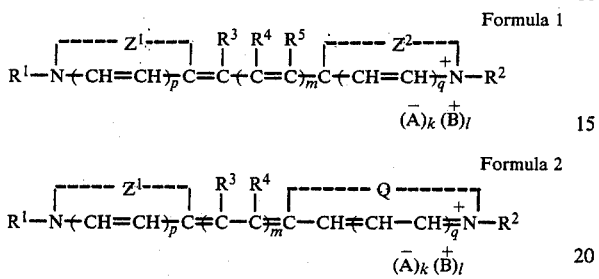

where
Z$^1$ and Z$^2$ may be the same or different and each represents the elements needed to complete a cyclic nucleus derived from basic heterocyclic nitrogen compounds such as oxazoline, oxazole, benzoxazole, the naphthoxazoles (e.g., naphth[2,1-d]oxazole, naphth[2,3-d]oxazole, and naphth[1,2-d]oxazole), oxadiazole, thiazoline, thiazole, benzothiazole, the naphthothiazoles (e.g., naphtho[2,1-d]thiazole), the thiazoloquinolines (e.g., thiazolo[4,5-b]quinoline), phenanthrothiazole, acenaphthothiazole, thiadioxazole, selenazoline, selenazole, benzoselenazole, the naphthoselenazoles (e.g., naphtho[1,2-d]selenazole), benzotellurazole, naphthotellurazoles (e.g., naptho[1,2-d]tellurazole), imidazoline, imidazole, benzimidazole, the naphthimidazoles (e.g., naphth[2,3-d]imidazole), 2- or 4-pyridine, 2- or 4-quinoline, 1- or 3-isoquinoline, benzoquinoline, 3H-indole, 1H- or 3H-benzoindole, and pyrazole, which nuclei may be substituted on the ring by one or more of a wide variety of substituents such as hydroxy, the halogens (e.g., fluoro, chloro, bromo, and iodo), alkyl groups or substituted alkyl groups (e.g., methyl, ethyl, propyl, isopropyl, butyl, octyl, dodecyl, octadecyl, 2-hydroxyethyl, 3-sulfopropyl, carboxymethyl, 2-cyanoethyl, and trifluoromethyl), aryl groups or substituted aryl groups (e.g., phenyl, 1-naphthyl, 2-naphthyl, 4-sulfophenyl, 3-carboxyphenyl, and 4-biphenylyl), aralkyl groups (e.g., benzyl and phenethyl), alkoxy groups (e.g., methoxy, ethoxy, and isopropoxy), aryloxy groups (e.g., phenoxy and 1-naphthoxy), alkylthio groups (e.g., methylthio and ethylthio), arylthio groups (e.g., phenylthio, p-tolythio, and 2-naphthylthio), methylenedioxy, cyano, 2-thienyl, styryl, amino or substituted amino groups (e.g., anilino, dimethylamino, diethylamino, and morpholino), and acyl groups, such as formyl, acetyl, benzoyl and benzenesulfonyl;

Q represents the elements needed to complete a cyclic nucleus derived from basic heterocyclic nitrogen compounds such as pyrrole, indole, carbazole, benzindole, pyrazole, indazole, and pyrrolopyridine;

R$^1$ and R$^2$ can be the same or different and represent alkyl groups, aryl groups, alkenyl groups, or aralkyl groups, with or without substituents, (e.g., carboxy, hydroxy, sulfo, alkoxy, sulfato, thiosulfato, phosphono, chloro, and bromo substituents);

R$^3$ represents hydrogen;

R$^4$ and R$^5$ represents hydrogen or alkyl of from 1 to 4 carbon atoms;

p and q are 0 or 1, except that both p and q preferably are not 1;

m is 0 or 1 except that when m is 1 both p and q are 0 and at least one of Z$^1$ and Z$^2$ represents imidazoline, oxazoline, thiazoline, or selenazoline;

A is an anionic group;

B is a cationic group; and k and l may be 0 or 1, depending on whether ionic substituents are present. Variants are, of course, possible in which R$^1$ and R$^3$, R$^2$ and R$^5$, or R$^1$ and R$^2$ (particularly when m, p, and q are 0) together represent the atoms necessary to complete an alkylene bridge.

Preferred shorter wavelength merocyanine dyes are zero methine merocyanines; however, useful shorter wavelength merocyanine dyes can be selected from among those of Formula 3.

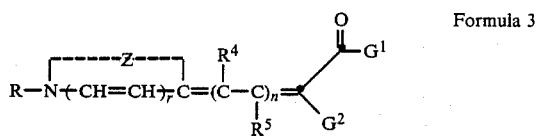

where
Z represents the same elements as either Z$^1$ or Z$^2$ of Formula 1 above;

R represents the same groups as either R$^1$ or R$^2$ of Formula 1 above;

R$^4$ and R$^5$ represent hydrogen, an alkyl group of 1 to 4 carbon atoms, or an aryl group (e.g., phenyl or naphthyl);

G$^1$ represents an alkyl group or substituted alkyl group, an aryl or substituted aryl group, an aralkyl group, an alkoxy group, an aryloxy group, a hydroxy group, an amino group, or a substituted amino group, wherein exemplary substituents can take the various forms noted in connection with Formula 1;

G$^2$ can represent any one of the groups listed for G$^1$ and in addition can represent a cyano group, an alkyl, or arylsulfonyl group, or a group represented by

or G$^2$ taken together with G$^1$ can represent the elements needed to complete a cyclic acidic nucleus such as those derived from 2,4-oxazolidinone (e.g., 3-ethyl-2,4-oxazolidindione), 2,4-thiazolidindione (e.g., 3-methyl-2,4-thiazolidindione), 2-thio-2,4-oxazolidindione (e.g., 3-phenyl-2-thio-2,4-oxazolidindione), rhodanine, such as 3-ethylrhodanine, 3-phenylrhodanine, 3-(3-dimethylaminopropyl)rhodanine, and 3-carboxymethylrhodanine, hydantoin (e.g., 1,3-diethylhydantoin and 3-ethyl-1-phenylhydantoin), 2-thiohydantoin (e.g., 1-ethyl-3-phenyl-2-thiohydantoin, 3-heptyl-1-phenyl-2-thiohydantoin, and 1,3-diphenyl-2- thiohydantoin), 2-pyrazolin-5-one, such as 3-methyl-1-phenyl-2-pyrazolin-5-one, 3-methyl-1-(4-carboxybutyl)-2-pyrazolin-5-one, and 3-methyl-2-(4-sulfophenyl)-2-pyrazolin-5-one, 2-isoxazolin-5-one (e.g., 3-phenyl-2-isoxazolin5-one), 3,5-pyrazolidindione (e.g., 1,2-diethyl-3,5-pyrazolidindione and 1,2-diphenyl-3,5-pyrazolidindione), 1,3-indandione, 1,3-dioxane-4,6-dione, 1,3-cyclohexanedione, barbituric acid (e.g., 1-ethylbarbituric acid and 1,3-diethylbarbituric acid), and 2-thiobarbituric acid (e.g., 1,3-diethyl-2-thiobarbituric acid and 1,3-bis(2-methoxyethyl)-2-thiobarbituric acid);

r and n each can be 0 or 1 except that when n is 1 then generally either Z is restricted to imidazoline, oxazoline, selenazoline, thiazoline, imidazoline, oxazole, or benzoxazole, or $G^1$ and $G^2$ do not represent a cyclic system.

Useful shorter wavelength hemicyanine dyes can be selected from among those represented by Formula 4.

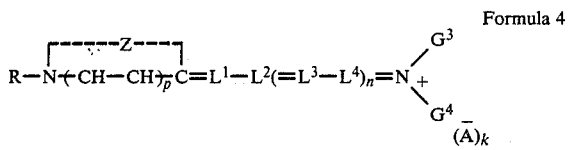

Formula 4 where

Z, R, and p represent the same elements as in Formula 2; $G^3$ and $G^4$ may be the same or different and may represent alkyl, substituted alkyl, aryl, substituted aryl, or aralkyl, the substituents being as illustrated for ring substituents in Formula 1 or $G^3$ and $G^4$ taken together complete a ring system derived from a cyclic secondary amine, such as pyrrolidine, 3-pyrroline, piperidine, piperazine (e.g., 4-methylpiperazine and 4-phenylpiperazine), morpholine, 1,2,3,4-tetrahydroquinoline, decahydroquinoline, 3-azabicyclo[3,2,2]nonane, indoline, azetidine, and hexahydroazepine;

$L^1$ to $L^4$ represent hydrogen, alkyl of 1 to 4 carbons, aryl, substituted aryl, or any two of $L^1$, $L^2$, $L^3$, $L^4$ can represent the elements needed to complete an alkylene or carbocyclic bridge;

n is 0 or 1; and

A and k have the same definition as in Formula 1.

Useful shorter wavelength hemioxonol dyes can be selected from among those represented by Formula 5.

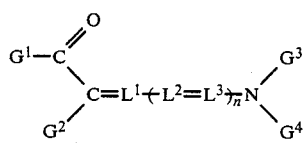

Formula 5 where $G^1$ and $G^2$ represent the same groups as in Formula 3;

$G^3$, $G^4$, $L^1$, $L^2$, and $L^3$ represent the same groups as in Formula 4; and n is 0 or 1.

Useful shorter wavelength merostyryl dyes can be selected from among those represented by Formula 6.

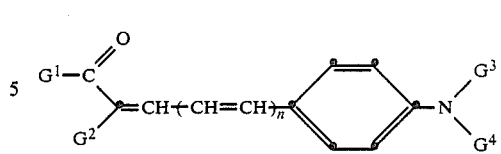

Formula 6 where $G^1$, $G^2$, $G^3$, $G^4$, and n are as defined in Formula 5.

Formulae 1 through 6 are intended merely as illustrative of cyanine, merocyanine, hemicyanine, hemioxonol, and merostyryl dyes from which useful shorter wavelength dyes from these classes can be selected, other selections of dyes from these classes and from among other known dyes and dye classes being possible. Further, the various substituents not forming a part of the dye chromophore can be varied as desired to tailor dye physical properties, particularly hydrophobicity and hydrophilicity, to suit the particular film forming components employed. By employing hydrocarbon groups having more carbon atoms (e.g., from about 6 to 20 carbon atoms) the dyes can be rendered more oleophilic while hydrocarbon groups containing fewer numbers of carbon atoms (e.g., 1 to 5 carbon atoms) and particularly those bearing polar substituents render the dyes more hydrophilic.

In addition to being a shorter wavelength dye as previously defined, to be useful as a photosensitizer in the present invention the dye must exhibit a reduction potential which is at most 0.1 volt more positive than the reduction potential of the azinium salt activator with which it is employed. Electron transfer from the photosensitizer to the activator is efficiently achieved when the reduction potential of the shorter wavelength dye is more negative than that of the photoactivator. In addition, when the reduction potentials of the photosensitizer and activator are equal, energy transfer can still occur. Further, effective performance has been observed when the reduction potential of the photosensitizer is more positive than that of the activator to a limited degree.

In order then to select suitable shorter wavelength dyes for the practice of the invention it is necessary to compare the reduction potentials of the azinium activator to be employed and the shorter wavelength dye. In the overwhelming majority of instances precise determinations of reduction potentials are not required to ascertain that the proper relationship of reduction potentials exists. In those few instances in which the reduction potential of the dye is sufficiently positive with respect to that of the activator that a precise determination of reduction potentials is desired, it must be taken into account that reduction potentials can vary as a function of the manner in which they are measured. To provide a specific standard for reduction potential determinations, the procedure is employed described by J. Lenhard, "Measurement of Reversible Electrode Potentials for Cyanine Dyes by the Use of Phase-Selective Second Harmonic AC Voltammetry", Journal of Imaging Science, Vol. 30, No. 1, January/February 1986.

In addition to being directed to the use of shorter wavelength dyes satisfying the reduction potential relationship set forth above this invention contemplates the use of those shorter wavelength keto dyes which exhibit a low intersystem crossing efficiency to a triplet state. Specifically, this intersystem crossing efficiency should be less than 10 percent. Stated another way, it is the recognition of the present invention that shorter wavelength dyes having limited excited state lifetimes are nevertheless efficient photosensitizers.

To provide the best possible correlation to the conditions of actual use, the intersystem crossing efficiencies are measured in the photoresist rather than in solution. The measurement of intersystem crossing efficiencies to a triplet state are generally known and reported in the art and form no part of this invention. Techniques for measurement of this parameter are well known in the art, as illustrated by Specht, Martic, and Farid, "A New Class of Triplet Sensitizers", *Tetrahedron*, Vol. 38, pp. 1203-1211, 1982, and the references therein cited.

Known azinium activators can be employed in the practice of this invention. The azinium activators disclosed by Jenkins et al U.S. Pat. No. Res. 27,922 and 27,925, Specht and Farid U.K. 2,083,832A, and *Research Disclosure*, Vol. 200, December 1980, Item 20036, each cited above, provide a variety of examples of useful azinium activators.

The azinium activators include an azinium nucleus, such as a pyridinium, diazinium, or triazinium nucleus. The azinium nucleus can include one or more aromatic rings, typically carbocyclic aromatic rings, fused with an azinium ring. In other words, the azinium nuclei include quinolinium, isoquinolinium, benzodiazinium, and naphthodiazonium nuclei. To achieve the highest attainable activation efficiencies per unit of weight it is preferred to employ monocyclic azinium nuclei.

A quaternizing substituent of a nitrogen atom in the azinium ring is capable of being released as a free radical upon electron transfer from the photosensitizer to the azinium activator. In one preferred form the quaternizing substituent is an oxy substituent. The oxy substituent (—O—R) which quaternizes a ring nitrogen atom of the azinium nucleus can be selected from among a variety of synthetically convenient oxy substituents. The moiety R can, for example, be an alkyl radical, such as methyl, ethyl, butyl, etc. the alkyl radical can be substituted. For example, arakyl (e.g. benzyl and phenethyl) and sulfoalkyl (e.g., sulfomethyl) radicals are contemplated. In another form R can be an acyl radical, such as an —C(O)—$R^1$ radical, where $R^I$ can take any of the varied forms of alkyl and aralkyl radicals described above. In addition $R^1$ can be an aryl radical, such as phenyl or naphthyl. The aryl radical can in turn be substituted. For example, $R^1$ can be a tolyl or xylyl radical. R typically contains from 1 to 18 carbon atoms, with alkyl moieties in each instance above preferably containing from 1 to 8 carbon atoms and aryl moieties in each instance above containing 6 to 10 carbon atoms. Highest activity levels have been realized when the oxy substituent (—O—R) contains 1 or 2 carbon atoms.

The azinium nuclei need include no substituent other than the quaternizing substituent. However, the presence of other substituents is not detrimental to the activity of the activators. While it is known to include azinium nuclei substituents to increase blue light absorption by the activator directly, substituents capable of performing this function are not required.

It is a specific advantage of this invention that the shorter wavelength dye photosensitizer can be relied upon for the absorption of blue light, and the azinium nuclei, apart from the quaternizing substituent, can be unsubstituted or, preferably, substituted with comparatively simple groups chosen for properties such as ease of synthetic or physical handling convenience, such as groups chosen from among substituted and unsubstituted aryl substituents of from 6 to 10 carbon atoms (e.g., phenyl or naphthyl) and substituted and unsubstituted alkyl and alkenyl groups of from 1 to 18 carbon atoms, preferably of from 1 to 8 carbon atoms. Activators free of a blue chromophore and therefore having limited ability to absorb blue light offer the advantage of improved stability when exposed to light including blue wavelengths during synthesis and/or handling. For example, these activators remain stable when synthesized and handled in unfiltered room light.

To the extent that substituents other than the quaternizing nitrogen atom substituent are present in the azinium salts employed, it is preferred that these substituents be electron withdrawing or neutral. When substituents other than the quaternizing nitrogen atom substituent are present which are electron donating, the effect is to shift the reduction potential of the activator to a more negative value. Since the photosensitizer has a reduction which in relation to that of the azinium salt activator is at most 0.1 volt more positive, it is apparent that electron donating substituents have the effect of limiting the selection of dyes which can be employed in combination as useful photosensitizers. However, there remain many dyes having sufficiently negative reduction potentials to be useful as photosensitizers in combination with azinium activators having electron donating substituents. Thus, a wide choice of substituents for the azinium salts employed in the present invention are possible. Subject to the considerations indicated above, suitable azinium ring substituents can be illustrated by any one or combination of the various substituents listed for the anilines described below.

Any convenient charge balancing counter-ion can be employed to complete the activator. Both weakly and highly dissociated counter-ions have been demonstrated to be useful. The counter-ion can be chosen for compatibility with the remaining components of the imaging system. For example, fluorinated carboxylate counter-ions, particularly perfluorinated carboxylate counter-ions, which are relatively undissociated, have been advantageously employed with azinium activators incorporated in oleophilic media, more specifically described below. Nevertheless, it is believed that highest levels of activity can be attributed to azinium activators which are ionically dissociated from charge balancing counter-ions in the imaging composition. While variances in ionic dissociation can be achieved by varied choices of solvents, film forming components, acidity, etc., in general higher levels of counter-ion dissociation occur with more electronegative counter-ions, such as hexafluorophosphate, tetrafluoroborate, perchlorate, para-toluenesulfonate, halide, sulfate, and similar electronegative anions.

In addition to activator and photosensitizer coinitiators it is additionally recognized that a third coinitiator, referred to as an enhancer, can optionally be included in the photoresist composition. As is the subject of concurrently filed, commonly assigned U.S. Ser. No. 933,657, titled ENHANCED IMAGING COMPOSITION CONTAINING AN AZINIUM ACTIVATOR, it has been discovered that the imaging response of the photoresist composition can be further improved by including as an enhancer coinitiator an aniline which is ring substituted with one or more groups capable of imparting a net Hammett sigma value derived electron withdrawing characteristic of at least +0.20 to the benzene ring. A positive Hammett sigma value is indicative of a substituent which is capable of rendering a phenyl ring electron withdrawing while a negative Hammett sigma value is indicative of a substituent which is capable of rendering a phenyl ring electron donating. Hydrogen is assigned a Hammett sigma value of zero. Lange's Handbook of Chemistry, 12th Ed., McGraw-Hill, 1979, Table 3-12, pp. 3-135 to 3-138, lists Hammett sigma values for a large number of commonly encountered substituents. By algebraically summing the Hammett sigma values of the various ring substituents of the aniline (that is, the ring substituents other than the one required amine substituent) the net Hammett value derived electron withdrawing characteristic of the ring substituents can be determined.

It is to be noted that the amine substituent forming the aniline is an electron donating substituent. For example, the Hammett sigma values of a primary amine group ($-NH_2$); secondary amine groups, such as alkylamino (e.g., $-NHCH_3$, $-NHCH_2CH_3$, and $-NH-n-C_4H_9$); and tertiary amine groups, such as dialkylamino (e.g., $-NCH_3$) range from $-0.04$ to $-0.83$, but are generally more negative than $-0.20$. While it is not intended to be bound by any particular theory to account for the increased effectiveness imparted by the aniline initiator enhancers, it is believed that the molecular polarization created by the presence of both electron donating and electron withdrawing groups attached to the phenyl ring of the aniline can play a role in the observed increase in initiation activity.

In a preferred form the aniline contains a single ring substituent exhibiting a Hammett sigma value of greater than $+0.20$. The following illustrative substituents, with meta position Hammett sigma values shown parenthetically, are illustrative of useful electron withdrawing substituents which can be employed as the sole aniline ring substituent: cyano ($\sigma = +0.61$), alkylcarbonyl substituents (e.g., acetyl $\sigma = +0.38$ and trifluoroacetyl $\sigma = +0.65$), arylcarbonyl substituents (e.g., phenylcarbonyl $\sigma = +0.34$), oxycarbonyl substituents, including alkoxycarbonyl and aryloxycarbonyl substituents (e.g., methoxycarbonyl $\sigma = +0.32$, ethoxycarbonyl $\sigma = +0.37$), nitro ($\sigma = +0.71$), thiocyanato ($\sigma = +0.63$), perhaloalkyl substituents (e.g., trichloromethyl $\sigma = +0.47$ and trifluoromethyl $\sigma = +0.47$), perfluoroalkylthio substituents (e.g., trifluoromethylthio $\sigma = +0.35$), sulfamoyl substituents, including alkylsulfamoyl and arylsulfamoyl substituents (e.g., sulfamoyl $\sigma = +0.46$), carbonylthio substituents (e.g., acetylthio $\sigma = +0.39$), carbamoylthio substituents (e.g., carbamoylthio $\sigma = +0.34$), oxythio substituents, including alkoxythio and aryloxythio substituents (e.g., methoxythio $\sigma = +0.52$), and sulfonyl substituents, including alkylsulfonyl and arylsulfonyl substituents (e.g., methylsulfonyl $\sigma = +0.68$ and phenylsulfonyl $\sigma = +0.67$). Multiple ring substitutions with these substituents are contemplated.

In addition to the highly electron withdrawing substituents identified above the aniline ring can, but need not, include ring substituents having Hammett sigma value derived electron withdrawing characteristics less positive than $+0.20$, provided a net Hammett sigma value derived electron withdrawing characteristic of at least $+0.20$ is maintained. Exemplary simple substituents and their published meta Hammett sigma values are primary and second alkyl substituents, such as methyl $\sigma = -0.07$, ethyl $\sigma = -0.07$, n-propyl $\sigma = -0.05$, i-propyl $\sigma = -0.07$, n-butyl $\sigma = -0.07$, and sec-butyl $\sigma = 0.07$. These alkyl substituents are synthetically convenient and therefore contemplated, though electron donating. Alkyl substituents containing tertiary carbon atoms and particularly tertiary alkyl groups tend to be even more highly electron donating and are not preferred. Aryl groups such as phenyl, α-naphthyl, and β-naphthyl groups are contemplated (e.g., phenyl $\sigma = +0.06$). Other useful and specifically contemplated hydrocarbon substituents include alkaryl substituents (e.g., p-methylphenyl), aralkyl substituents (e.g., benzyl $\sigma = 0.05$ and phenethyl), alkenyl substituents (e.g. vinyl $\sigma = +0.02$), aralkenyl substituents (e.g., 2-phenylvinyl $\sigma = +0.14$), alkynyl substituents (e.g., ethynyl $\sigma = +0.21$, propargyl, and 2-butynyl), and aralkynyl substituents (e.g., phenethynyl $\sigma = +0.14$). Substituted hydrocarbon substituents are also contemplated, such as haloalkyl substituents (e.g., bromomethyl, chloromethyl $\sigma = -0.12$, fluoromethyl, and iodomethyl), haloaryl substituents (e.g., p-bromophenyl, m-bromophenyl, and p-chlorophenyl, and hydroxyalkyl substituents (e.g., hydroxymethyl $\sigma = +0.08$). Oxy substituents or substituent moieties of hydrocarbon substituents are specifically contemplated—i.e., hydroxy ($\sigma = +0.10$), alkoxy (e.g., methoxy $\sigma = +0.14$, ethoxy $\sigma = +0.07$, n-propoxy $\sigma = 0.07$, i-propoxy $\sigma = 0.00$, n-butoxy $\sigma = -0.05$, cyclohexoxy $\sigma = +0.29$, cyclohexylmethoxy $\sigma = +0.18$, and trifluoromethoxy $\sigma = +0.36$), and aryloxy (e.g., phenoxy $\sigma = +0.25$). Halogen substituents are contemplated—i.e., bromo ($\sigma = +0.39$), chloro ($\sigma = +0.35$), fluoro ($\sigma = +0.34$), and iodo ($\sigma = +0.35$). Amido substituents are also contemplated, such as amido ($\sigma = +0.25$), methylamido ($\sigma = +0.21$), phenylamido ($\sigma = +0.22$), and ureido ($\sigma = +0.18$).

When electron donating or weakly electron withdrawing substituents are employed, they are in every instance employed in combination so that the net Hammett sigma derived value of the various substituents other than the one required amino substituent forming the aniline is greater than $+0.20$. While meta position Hammett sigma values have been provided, in most instances para position Hammett sigma values are not highly different and can, in any event, be determined by reference to published lists. Ortho Hammett sigma values are usually essentially identical to para position Hammett sigma values. Meta, ortho, and para positions for the various substituents to the aniline are assigned with reference to the position of the amino group forming the aniline. To minimize molecular bulk it is generally preferred that the aliphatic moieties of the various ring substituents each contain 6 or fewer carbon atoms and that the aromatic moieties each contain 10 or fewer carbon atoms.

The organic film forming component of the negative-working photoresist to be acted upon by the coinitiators can take the form of any conventional negative-working photoresist organic film forming component containing ethylenic unsaturation and capable of selective immobilization by undergoing an addition reaction at the site of the ethylenic unsaturation. Immobilization can be imparted by initiating polymerization of monomers containing ethylenic unsaturation or by initiating crosslinking of linear polymers or oligomers containing ethylenic unsaturation. For example, any of the monomeric or crosslinkable polymeric film forming components disclosed in Jenkins et al U.S. Pat. No. Re. 27,925 or 27,922, respectively, are suitable for use in the photoresists of this invention and here incorporated by reference. Tan et al U.S. Pat. No. 4,289,842, here incorporated by reference, discloses negative working photoresists containing light sensitive acrylate copolymers containing pendant groups, such as alkenyl group with ethylenic unsaturation. Lindley U.S. Pat. No. 4,590,147, here incorporated by reference, discloses vinyl oligomers which can be employed as film forming components in the photoresists of this invention. Useful film forming components containing vinyl monomers are disclosed in Fuerniss U.S. Pat. No. 4,497,889 and Anderson et al U.S. Pat. No. 4,535,052, both here incorporated by reference. Kosar *Light-Sensitive Systems*, John Wiley & Sons, 1965, further describes a variety of useful film forming components for use in the practice of this invention, including ethylenically unsaturated monomers and polymers.

Preferred film forming components are comprised of at least one addition polymerizable ethylenically unsaturated compound having a boiling point above 100° C. at normal pressure which is preferably employed in combination with a polymeric binder. The ethylenically unsaturated compound (typically a monomer) and the polymeric binder can be employed together in widely varying proportions, including ethylenically unsaturated compound ranging from 3 to 97 percent by weight of the film forming component and polymeric binder ranging from 97 to 3 percent by weight of the film forming component. A separate polymeric binder, though preferred, is not an essential part of the film forming component and is most commonly omitted when the ethenically unsaturated compound is itself a polymer.

Chang U.S. Pat. No. 3,756,827, here incorporated by reference, discloses in column 2, line 36 to column 3, line 30, a variety of suitable organic monomers for use in the photoresists of this invention. Specifically illustrated in the examples below are ester monomers containing ethylenic unsaturation. Similar monomers include ethylenically unsaturated diester polyhydroxy polyethers, described in Chambers U.S. Pat. No. 4,245,031, here incorporated by reference.

Organic polymeric binders which can form a part of the film forming component of the photoresist include: (1) polyesters, including those based on terephthalic, isophthalic, sebacic, adipic, and hexahydroterephthalic acids; (2) nylons or polyamides; (3) cellulose ethers and esters; (4) polyaldehydes; (5) high molecular weight ethylene oxide polymers—e.g., poly(ethylene glycols), having weight average molecular weights from 4000 to 4,000,000; (6) polyurethanes; (7) polycarbonates; (8) synthetic rubbers—e.g., homopolymers and copolymers of butadienes; and (9) homopolymers and copolymers formed from monomers containing ethylenic unsaturation, such as polymerized forms of any of the various ethylenically unsaturated monomers which can be incorporated in the photoresists, such as polyalkylenes—e.g. polyethylene and polypropylene; poly(vinyl alcohol); poly(vinyl esters)—e.g., poly(vinyl acetate); polystyrene; poly(acrylic and methacrylic acids and esters)—e.g., poly(methyl methacrylate) and poly(ethyl acrylate), as well as copolymer variants.

The foregoing is, of course, only an illustrative listing of the most commonly encountered film forming components. Other specific illustrative film forming components are included in the examples.

In addition to the film forming component and the coinitiators the photoresists can contain any one or combination of known addenda, such as thermal inhibitors, colorants, plasticizers, fillers, etc. To facilitate coating on a substrate the film forming component, coinitiators, and addenda, if any, are usually dispersed in a solvent to create a solution or slurry, the liquid being evaporatively removed after coating. Any solvent can be employed for this purpose which is inert toward the film forming components and addenda of the photoresist. Solvents can be chosen from among a wide variety of organic liquids, including N,N-dimethylformamide; N,N-dimethylacetamide; alcohols, such as methanol, ethanol, butanol, etc.; ketones, such as acetone, cyclohexanone, and butanone; esters, such as ethyl acetate and ethyl benzoate; ethers, such as tetrahydrofuran and dioxane; chlorinated aliphatic hydrocarbons, such as methylene chloride and 1,2-dichloroethane; aromatic hydrocarbons, such as benzene and toluene; and other common solvents, such as dimethyl sulfoxide, chlorobenzene, and various mixtures of solvents.

The substrate onto which the photoresist is coated can take any convenient conventional form. For example, the photoresist can be used to define a pattern during fabrication of an electronic component. In this instance the substrate can take the form of a printed circuit board or semiconductor chip, typically one which has been only partially fabricated to a completed form. In other instances photoresists can be coated on simple unitary substrates, such as glass, ceramic, metal, cellulose paper, fiberboard, or polymer substrates. Specific substrates include alumina-blasted aluminum, anodized aluminum, alumina-blasted poly(ethylene terephthalate) film, poly(ethylene terephthalate) film, flame or electrostatic discharge treated poly(ethylene terephthalate) film, poly(vinyl alcohol)-coated paper, crosslinked polyester-coated paper, nylon, glass, cellulose acetate film, heavy paper, such as lithographic paper, and the like. Another specifically contemplated use of the photoresists of this invention is as a planarizing layer, such as a planarizing layer on a semiconductor chip or on an optical disc.

In perhaps their most commonly used form photoresists are coated in a fluid form on a substrate and evaporatively dried, usually with heating, to produce a uniform coating. Often, particularly in the manufacture of semiconductor devices, the substrate is spun, thereby employing centifugal forces to assure the uniformity of the photoresist coating before drying. After exposure to actinic radiation causes addition to occur at the ethylenic unsaturation sites of the film forming component, a liquid developer is brought into contact with the coated substrate to remove selectively the photoresist in areas which were not exposed to actinic radiation.

The liquid developer can be any convenient liquid which is capable of selectively removing the photoresist in unexposed areas. The coated photoresist can be sprayed, flushed, swabbed, soaked, or otherwise treated with the developer to achieve selective removal. In its simplest form the liquid developer can be the same liquid employed as a solvent in coating the photoresist. Methoxyethyl acetate and ethoxyethyl acetate are common developers. Also aqueous developers are commonly employed, such as miscible combinations of water and alcohols, with proportions in the range of from 20 to 80 percent water and 80 to 20 percent alcohol being common. Exemplary water miscible alcohols include glycerol, benzyl alcohol, 1,2-propanediol, sec-butyl alcohol, and ethers derived from glycols, such as dihydroxy poly(alkylene oxides). Lactone developers, such as those disclosed by Martinson et al U.S. Pat. No. 3,707,373, can be employed. Optimum developer choices for specific photoresists are disclosed in the various patents cited above illustrating the specific film forming components.

In forming planarizing layers the photoresist is spun after coating. The centrifugal forces level or at least reduce the relief of the surface of the coating. For optical disc planarizing layers highly smooth and defect free surfaces are required. For semiconductor manufacture planarizing layers are generally relied upon merely to reduce the surface relief. In either case, there is uniform exposure to actinic radiation, at least in the areas where the planarizing layer is desired. Where the entire photoresist coating is exposed to actinic radiation, there is, of course, no need for development, since there is no removal of the coating.

In still another manner of use, a photoresist layer is coated on a support and overcoated with a strippable cover sheet. The end user typically purchases the photoresist as an article rather than a liquid composition. After removing the cover sheet, the photoresist layer together with its support is laminated to the substrate on which the image pattern is desired. Following patterned exposure to actinic radiation through the support, the support is stripped from the substrate leaving photoresist on the substrate in an imagewise pattern.

In still another manner of use the photoresist is coated on a support surface modified to facilitate electroless metal deposition. Again, a strippable cover sheet is located on the photoresist coating. In this use imagewise exposure to actinic radiation occurs through the cover sheet followed by stripping. Upon stripping of the cover sheet there is selective removal of the photoresist so that remaining photoresist defines the desired pattern. Electroless metal plating can then be undertaken to convert the support into an article having a metal pattern thereon. A common application is in the formation of electrical circuits.

The common feature of all of these applications is that the film forming component of the photoresist with the coinitiators present forms a coating which is then exposed to actinic radiation. The actinic radiation that is employed with the photoresist of this invention is electromagnetic radiation including wavelengths in at least the blue region of the spectrum. By employing shorter wavelength dyes as photosensitizers the photoresists are rendered highly sensitive to blue light. By employing visible light for exposures visual corroboration of exposure is possible. Further, source elements for blue light exposures offer construction advantages over the conventionally employed ultraviolet exposure sources.

Any conventional ratio of activator to film forming component can be present in the photoresists of this invention. Activator concentrations are as a practical matter most conveniently specified in terms of moles of activator per gram of dry solids, the latter consisting of the film forming component and the minor amounts of various addenda, but excluding any liquid component introduced to facilitate coating. Typically from about $2 \times 10^{-5}$ to $25 \times 10^{-5}$, most preferably from about $5 \times 10^{-5}$ to $20 \times 10^{-5}$ mole of activator is present per gram of dry solids.

In the practice of the present invention the enhancer is an optional coinitiator, meaning that it need not be present or need not be present in an effective amount. However, it is generally preferred to incorporate the enhancer in any convenient effective amount. Typically from about 0.1 to 10 moles per mole of activator are employed. The use of larger amounts is, of course, possible.

The photosensitizer can be present in any concentration capable of increasing the response of the photoresist to blue light. While the photosensitizer concentration can vary widely, it is generally contemplated to employ photosensitizer in concentrations ranging from about $5 \times 10^{-7}$ to $1 \times 10^{-4}$ mole per gram of dry solids. Preferred photosensitizer concentrations are in the range of from $10^{-6}$ to $5 \times 10^{-5}$ mole per gram of dry solids, with optimum concentrations generally being in the range of from about $2 \times 10^{-6}$ to $2 \times 10^{-5}$ mole per gram of dry solids.

EXAMPLES

The invention can be better appreciated by reference to the following specific examples.

EXAMPLES 1 THROUGH 35

A series of negative working photoresist compositions PR-1 each containing 0.02 millimole of a different dye being tested as a photosensitizer were prepared.

PR-1 was formulated as follows:
2.34 g Binder A
1.17 g Monomer A
1.17 g Monomer B
0.012 g Inhibitor A
0.077 g Activator A
0.02 mmol Photosensitizer
10.32 g Solvent (Dichloromethane)

Binder A exhibited the following structure

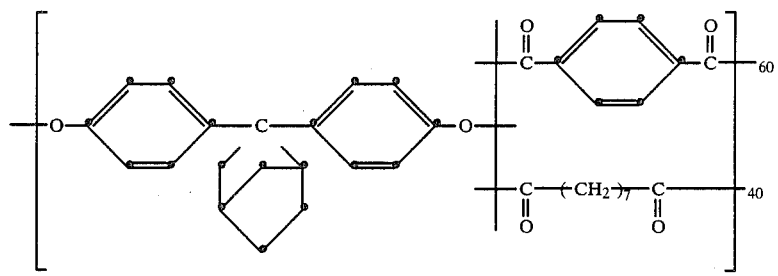

Monomer A exhibited the following structure

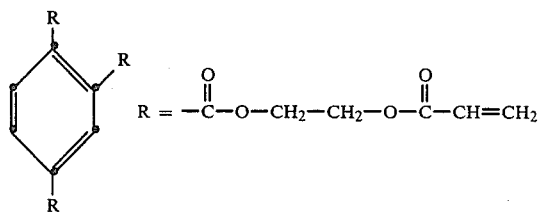

Monomer B exhibited the following structure

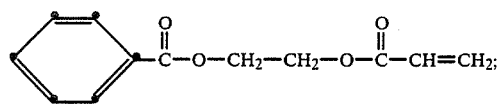

Inhibitor A exhibited the following structure

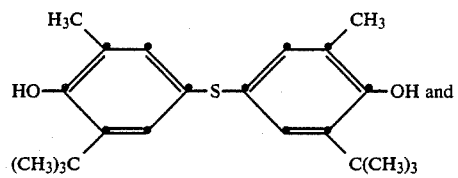

Activator A was 1-methoxy-4-phenylpyridinium tetrafluoroborate.

Each of the photoresist compositions was coated on a copper sheet using a 0.3 mm coating knife and dried for 10 minutes at about 70° C. A transparent polypropylene cover sheet was then placed over the coating.

Since PR-1 without the photosensitizer coinitiator responds to ultraviolet exposures, shorter wavelengths were removed during exposure using filters. Specifically, wavelengths below the absorption peak of the photosensitizer dye were removed using a W-2A, W-16, or W-25 Wratten ® filter capable of filtering 99.9 percent of radiation of less than 400, 510, or 580 nm in wavelength, respectively.

To determine the degree of effectiveness of the photosensitizer exposure of each coated sample was undertaken through a Kodak T-14 ® step tablet having 14 equal increment density steps ranging in density from essentially zero to 2.1. Three minute exposures were undertaken using a Nu-arc FT32L ® flip-top platemaker equipped with a 4000 watt pulsed Xenon lamp. After exposure the samples were baked for 10 minutes at 70° C. and spray developed for two minutes. Development was undertaken using 1,1,1-trichloroethane as a developer. Response was measured in terms of the number of stepped exposure areas (steps) in which the photoresist was retained following exposure. For example, a photoresist sample which was retained following exposure and development on 10 steps, but was absent from the remaining four steps was assigned a step rating of 10. If partial retention of the photoresist was observed on the eleventh step, this was indicated by assigning a plus rating—i.e., 10+. On the other hand, where the photoresist retention was deemed just barely adequate to merit the step rating, this was indicated by assigning a minus rating—i.e., 10—.

Results with the various dyes are indicated below in Table I, which reports the absorption peak of the dye in the coating and the step range of response. Activator A exhibited a reduction potential of −0.75 volt, and each of the dye photosensitizers exhibited a reduction potential less than 0.1 volt more positive than the reduction potential of Activator A.

When control formulations of PR-1 were prepared varied only by omitting Activator A, so that the dye was the sole initiator present, little or no imaging response was observed. This showed the dye photosensitizers to be relatively ineffective when employed as the sole initiators.

When control formulations of PR-1 were prepared varied only by omitting the dye, so that Activator A was the sole initiator present, performance of the procedure described above and including the filtering used with the dyes resulted in no imaging response being observed. This showed the activator to be ineffective to impart sensitivity to the photoresist in the blue portion of the spectrum.

The dyes employed as photosensitizers, their reduction potentials, and the number of steps of retained photoresist after development are shown in Table I. In every instance the keto dyes listed in Table I exhibit an intersystem crossing efficiency to a triplet state of less than 10 percent.

TABLE I

|      | R            | X⁻   | λ-max | $E_{red}$ | Steps |
|------|--------------|------|-------|-----------|-------|
| PS-1 | —C₁₆H₃₃      | I⁻   | 430   | −1.45     | 6⁺    |
| PS-2 | —C₁₈H₃₇      | PTS⁻ | 432   | −1.45     | 6⁻    |
| PS-3 | —CH₂CH=CH₂   | Br⁻  | 432   | ca−1.45   | 7     |

PTS = p-toluene sulfonate

| PS-4 | | | 453 | −1.28 | 6⁺ |
| PS-5 | | | 503 | | 7⁺* |

TABLE I-continued

[Structure of bis-quinoline cyanine dye with N-R groups and X⁻ counterion]

| | R | X⁻ | λ-max | E_red | Steps |
|---|---|---|---|---|---|
| PS-6 | —CH₂CH₃ | I⁻ | 532 | −1.13 | 2 |
| PS-7 | —C₄H₉ | I⁻ | 532 | −1.13 | 2 |
| PS-8 | —C₅H₁₁ | I⁻ | 532 | −1.13 | 2 |

PS-9 [structure with N-CH₂CH₃, N-CH₃, C₆H₅, Cl⁻]  502  −1.30  10*

PS-10 [benzoxazolium structure with N-CH₂CH₃, ClO₄⁻]  484  −1.36  9*

PS-11 [benzoxazolium structure with N-CH₂CH₃, ClO₄⁻]  485  ca−1.36  10*

PS-12 [bis-benzoxazole structure with N-C₆H₁₃ groups, I⁻]  499  −1.30  10⁺*

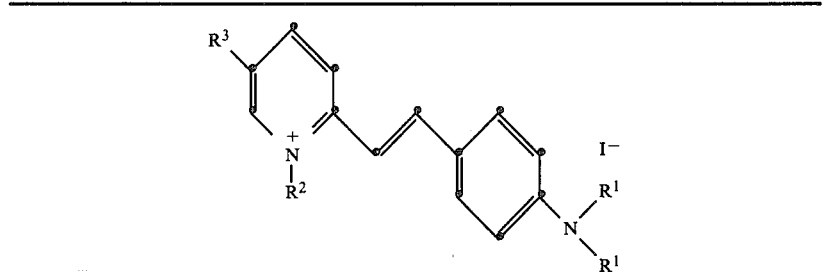

| | R¹ | R² | R³ | λ-max | E_red | Steps |
|---|---|---|---|---|---|---|
| PS-13 | —CH₃ | —CH₃ | H | 468 | −1.19 | 10⁺* |
| PS-14 | —CH₃ | —CH₃ | —C₂H₃ | 462 | −1.09 | 12⁻* |
| PS-15 | —C₃H₇ | —CH₃ | H | 480 | −1.23 | 12⁻* |

TABLE I-continued
PS-16 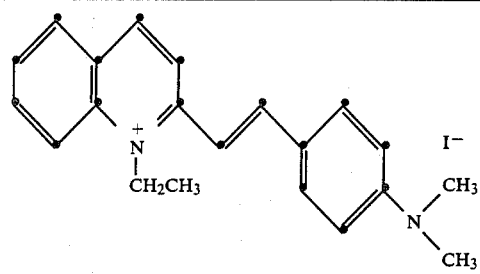 535 −0.88 8*
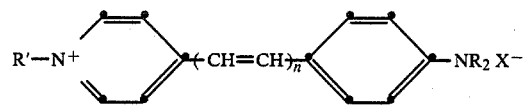
| | n | R' | R | X− | λ-max | $E_{red}$ | Steps |
|---|---|---|---|---|---|---|---|
| PS-17 | 1 | —CH$_3$ | C$_2$H$_5$ | I− | 494 | −1.1 | 11+* |
| PS-18 | 1 | (CH$_2$)$_3$SO$_3$— | C$_5$H$_{11}$ | — | 496 | −1.14 | 12+* |
| PS-19 | 1 | (CH$_2$)$_4$SO$_3$— | C$_5$H$_{11}$ | — | 497 | −1.14 | 12+* |
| PS-20 | 2 | (CH$_2$)$_4$SO$_3$— | C$_5$H$_{11}$ | — | 508 | −1.07 | 10+* |
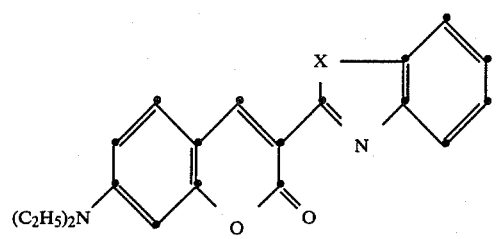
| | | λ-max | $E_{red}$ | Steps |
|---|---|---|---|---|
| PS-21 | X = S | 467 | −1.36 | 11−* |
| PS-22 | X = NH | 450 | −1.48 | 10− |
| PS-23 | X = NCH$_3$ | 420 | −1.60 | 10+ |
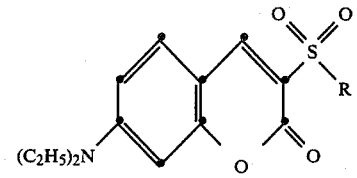
| | R | λ-max | $E_{red}$ | Steps |
|---|---|---|---|---|
| PS-24 | C$_6$H$_5$ | 423 | ca−1.4 | 10−* |
| PS-25 | —CH$_3$ | 415 | −1.5 | 9 |
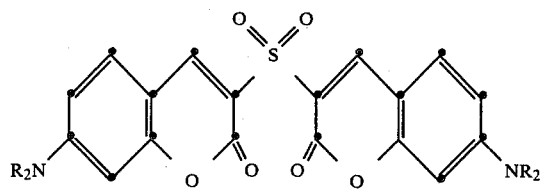
| | R | λ-max | $E_{red}$ | Steps |
|---|---|---|---|---|
| PS-26 | R = CH$_2$CH$_3$ | 447 | ca−1.4 | 12+* |
| PS-27 | R = CH$_2$CH$_2$CH$_3$ | 449 | ca−1.4 | 13−* |
| | λ-max | Steps |
|---|---|---|
| PS-28 | 435 | 11 |
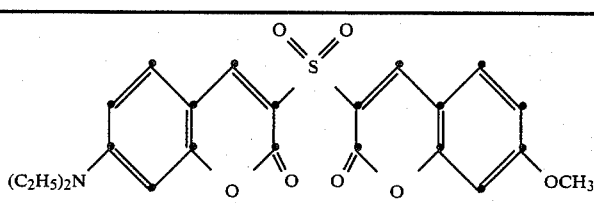

TABLE I-continued
PS-29  460 13
PS-30 410 4
9,10-diethoxyanthracene
| | | | | | | λ-max | $E_{red}$ | Steps |
|---|---|---|---|---|---|---|---|---|
| PS-31 | | | | | | 453 | −1.5 | 10* |
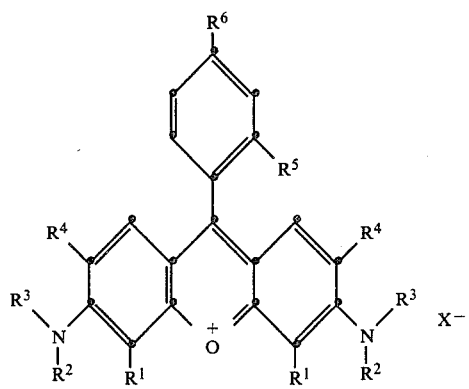
| | $R^1$ | $R^2$ | $R^3$ | $R^4$ | $R^5$ | $R^6$ | $X^-$ | λ-max | $E_{red}$ | Steps |
|---|---|---|---|---|---|---|---|---|---|---|
| PS-32 | H | —CH$_2$CH$_3$ | H | —CH$_3$ | COOCH$_2$CH$_3$ | H | Cl$^-$ | 535 | −0.82 | 5+ |
| PS-33 | H | —CH$_2$CH$_3$ | H | —CH$_3$ | COOCH$_2$CH$_3$ | H | BF$_4^-$ | 535 | −0.82 | 7−* |
| | | λ-max | $E_{red}$ | Steps |
|---|---|---|---|---|
| PS-34 | acridine orange | 502 | | 10 |
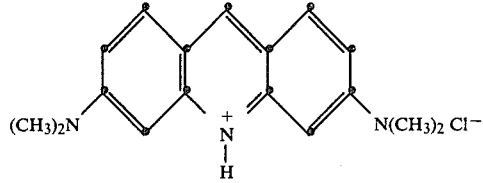

TABLE I-continued

| | | | | |
|---|---|---|---|---|
| PS-35 | 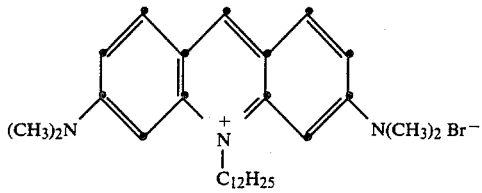 | 503 | −1.1 | 10+* |

EXAMPLES 36 THROUGH 55

Most of the experiments reported in Examples 1 through 35 were repeated, but with the coated samples held for more than 6 months. In comparing performances of fresh coated samples with those stored at room temperature for more than 6 months no variances in the number of steps developed was observed or at most variances of only one step. These observations were made using the dyes represented by the asterisks in Tables I.

These examples illustrate the outstanding stability of the imaging compositions and, particularly, the photosensitizer coinitiators of this invention.

EXAMPLES 56 THROUGH 65

The procedure of Examples 1 through 35 was repeated, but with a variety of differing azinium activators substituted for Activator A. The photoresist contained photosensitizer PS-26. The results are listed below in Table II. All of the azinium activators were effective. When no azinium activator was present in the photoresist, all of the photoresist was removed on development. In other words, the number of steps was zero.

TABLE II

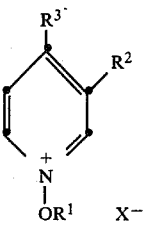

| $R^1$ | $R^2$ | $R^3$ | $X^-$ | Steps |
|---|---|---|---|---|
| $CH_3$ | H | $C_6H_5$ | $BF_4^-$ | 12+ |
| $CH_3$ | H | $C_6H_5$ | $C_3F_7COO^-$ | 9 |
| $CH_3$ | H | CN | $BF_4^-$ | 9+ |
| $CH_3$ | H | $COOCH_3$ | $PF_6^-$ | 11− |
| $CH_3$ | H | $COOCH_2CH_2C_6H_5$ | $BF_4^-$ | 10+ |
| $CH_3$ | $COOCH_3$ | H | $PF_6^-$ | 13− |
| $CH_3$ | $COOCH_2CH_2C_6H_5$ | H | $PF_6^-$ | 12+ |
| $CH_3$ | $COOCH_2CH_2C_6H_5$ | H | $BF_4^-$ | 11+ |
| $CH_3$ | $COOCH_2CH_2OC_2H_5$ | H | $BF_4^-$ | 12+ |
| $C_2H_5$ | H | $C_6H_5$ | $BF_4^-$ | 10+ |

APPENDIX

The dyes employed as photosensitizers can be selected from among conventional dyes, the preparation of which is generally known. However, since dyes PS-24, PS-26, and PS-27 are novel, an exemplary preparation for each of these dyes is included.

A. Preparation of 7-Diethylamino-3-phenylsulfonylcoumarin (PS-24)

A mixture of 1 g (0.0052 mole) 4-diethylaminosalicylaldehyde and 1 g (0.004 mole) ethyl 2-phenylsulfonyl acetate in 5 mL ethyl alcohol was heated until the aldehyde dissolved. Piperidine (10 drops) was added and the reaction mixture was heated at reflux on a steam bath for 1¾ hours. After chilling in the freezer, the product was collected and recrystallized twice from ethyl alcohol/acetonitrile.

NMR(CDCl$_3$) ($\delta$) 1.22 (t, —CH$_3$), 3.45 (q, —CH$_2$—), 6.40 (d, H—8, J=2.4 Hz), 6.63 (dd, H—5, J$_{5-6}$=9 Hz J$_{6-8}$=2.4 Hz) 7.32–7.67 (m, H—5, 3', 4') 8.02–8.22 (m, H—2'), 8.53 (s, H—4)

B. Preparation of 3,3'-sulfonylbis(7-diethylaminocoumarin) (PS-26)

A solution of 12 g (0.062 mole) 4-diethylaminosalicylaldehyde, 5 g (0.024 mole) dimethyl 2,2'-sulfonyldiacetate, 100 mL ethyl alcohol and 3.3 mL piperidine was heated at reflux on a steam bath for 1 hour. The reaction mixture was chilled, the product collected and recrystallized twice from a mixture of 300 mL ethyl alcohol/100 mL acetonitrile. Yield 7.0 g.

NMR(CDCl$_3$) ($\delta$) 1.22 (t, —CH$_3$), 3.45 (q, N—CH$_2$), 6.45 (br, s, H—8,8') 6.65 (br. d, H—6,6'), 7.45 (d, H—5,5'), 8.65 (br. s, H—4,4')

C. Preparation of 3,3'-Sulfonylbis(7-dipropylaminocoumarin) (PS-27)

A solution of 2 g (0.0103 mole) of 4-di-n-propylamino salicylaldehyde, 1 g (0.0042 mole) of dimethyl 2,2'-sulfonyldiacetate, 50 mL of ethyl alcohol and 0.5 mL piperidine was stirred overnight at room temperature then heated at reflux on a steam bath for 6 hours. The reaction mixture was chilled in a freezer and the solid collected. The product was recrystallized three times from a mixture of ethyl alcohol/acetonitrile. Yield 0.35 g.

NMR(CDCl$_3$) ($\delta$) 0.95 (t, —CH$_3$), 1.62 (m, —CH$_2$—), 3.33 (t, N—CH$_2$), 6.40 (br. s, H—8,8'), 6.60 (br. d, H—6,6'), 7.43 (d, H—5,5'), 8.63 (s, H—4,4').

The invention has been described in detail with particular reference to preferred embodiments thereof, but it will be understood that variations and modifications can be effected within the spirit and scope of the invention.

What is claimed is:

1. A negative working photoresist responsive to imaging radiation of a wavelength longer than 550 nm consisting essentially of
    an organic film forming component chosen from the class consisting of monomers, oligomers, and polymers each containing ethylenic unsaturation and capable of selective immobilization by addition at the site of ethylenic unsaturation and
    coinitiators for ethylenic addition comprised of
    an effective amount of a quaternized azinium salt activator and
    a concentration sufficient to increase response of the photoresist to light of a photosensitizer which is a dye having its principal absorption peak at a wavelength shorter than 550 nm and having a reduction potential which in relation to that of said azinium salt activator is at most 0.1 volt more positive, with the further proviso that, when said dye is a keto dye, it exhibits when excited by imaging radiation an intersystem crossing efficiency to a triplet state of less than 10 percent.

2. A negative working photoresist according to claim 1 in which said organic film forming component is comprised of at least one addition polymerizable ethylenically unsaturated compound having a boiling point above 100° C. at normal pressure.

3. A negative working photoresist according to claim 2 in which said polymerizable ethylenically unsaturated compound is a monomer.

4. A negative working photoresist according to claim 2 in which said polymerizable ethylenically unsaturated compound is an oligomer.

5. A negative working photoresist according to claim 2 in which said polymerizable ethylenically unsaturated compound is a crosslinkable polymer.

6. A negative working photoresist according to claim 2 in which said organic film forming component additionally includes a binder.

7. A negative working photoresist according to claim 1 in which said photosensitizer exhibits a reduction potential that is more negative than the reduction potential of said azinium activator.

8. A negative working photoresist according to claim 1 in which said photosensitizer is a non-keto methine dye.

9. A negative working photoresist according to claim 1 in which said photosensitizer is a cyanine dye.

10. A negative working photoresist according to claim 1 in which said photosensitizer is an anthracene dye or a rhodamine dye.

11. A negative working photoresist according to claim 1 in which said photosensitizer is a coumarin dye which exhibits an intersystem crossing efficiency to a triplet state of less than 10 percent.

12. An article comprised of a substrate and a negative working photoresist coating consisting essentially of
    an organic film forming component chosen from the class consisting of monomers, oligomers, and polymers each containing ethylenic unsaturation and capable of selective immobilization by addition at the site of ethylenic unsaturation and
    coinitiators for ethylenic addition comprised of
    an effective amount of a quaternized azinium salt activator and
    a concentration sufficient to increase response of the photoresist to light of a photosensitizer which is a dye having its principal absorption peak at a wavelength shorter than 550 nm and having a reduction potential which in relation to that of said azinium salt activator is at most 0.1 volt more positive, with the further proviso that, when said dye is a keto dye, it exhibits when excited by imaging radiation an intersystem crossing efficiency to a triplet state of less than 10 percent.

13. A negative working photoresist according to claim 1 wherein said photosensitizer is present in a concentration ranging from $5 \times 10^{-7}$ to $1 \times 10^{-4}$ mole per gram of dry solids.

14. A negative working photoresist according to claim 13 where said activator is present in a concentration of from $2 \times 10^{-5}$ to $25 \times 10^{-5}$ mole per gram of dry solids.

15. An article according to claim 12 in which said organic film forming component is comprised of at least one addition polymerizable ethylenically unsaturated compound having a boiling point about 100° C. at normal pressure.

16. An article according to claim 12 in which said photosensitizer exhibits a reduction potential that is more negative than the reduction potential of said azinium activator.

17. An article according to claim 12 in which said photosensitizer is a non-keto methine dye.

18. An article according to claim 12 in which said photosensitizer is a cyanine dye.

19. An article according to claim 1 in which said photosensitizer is an anthracene dye or a rhodamine dye.

20. An article according to claim 12 in said photosensitizer is a coumarin dye which exhibits an intersystem crossing efficiency to a triplet state of less than 10 percent.

21. An article according to claim 12 wherein said photosensitizer is present in a concentration ranging from $10^{-6}$ to $5 \times 10^{-5}$ mole per gram of dry solids.

22. An article according to claim 21 wherein said photosensitizer is present in a concentration ranging from $2 \times 10^{-6}$ to $2 \times 10^{-5}$ mole per gram of dry solids.

23. An article according to claim 21 wherein said activator is present in a concentration of from $5 \times 10^{-5}$ to $20 \times 10^{-5}$ mole per gram of dry solids.

24. A photoresist composition according to claim 1 wherein said azinium salt activator is free of a dye chromophore and is stable in unfiltered room light.

25. An article according to claim 12 wherein said azinium salt activator is free of a dye chromophore and is stable in unfiltered room light.

26. A photoresist composition according to claim 1 wherein said photosensitizer is a dye having its principal absorption peak in the visible portion of the spectrum.

27. An article according to claim 12 wherein said photosensitizer is a dye has its principal absorption peak in the visible portion of the spectrum.

28. A photoresist composition according to claim 26 wherein said photosensitizer is a magenta dye.

29. An article according to claim 28 wherein said photosensitizer is magenta dye.

* * * * *